United States Patent [19]

Mikhail

[11] Patent Number: 5,397,330
[45] Date of Patent: Mar. 14, 1995

[54] POSTERIOR CRUCIATE LIGAMENT RETRACTOR FOR USE IN PERFORMING KNEE SURGERY

[76] Inventor: E. Michael Mikhail, 4203 Shamley Green, Toledo, Ohio 43623

[21] Appl. No.: 193,253

[22] Filed: Feb. 8, 1994

Related U.S. Application Data

[62] Division of Ser. No. 988,205, Dec. 9, 1992, Pat. No. 5,334,194, which is a division of Ser. No. 508,090, Apr. 11, 1990, Pat. No. 5,217,463.

[51] Int. Cl.⁶ ............................................. A61B 17/56
[52] U.S. Cl. ........................................ 606/88; 606/86; 606/53; 128/20
[58] Field of Search ............... 606/53, 60, 62, 86-90, 606/99, 105; D7/653; 7/112; 30/322; 128/20

[56] References Cited

U.S. PATENT DOCUMENTS

| | | |
|---|---|---|
| D. 245,918 | 9/1977 | Shen . |
| 1,313,417 | 8/1919 | Raymond ........................... 7/112 |
| 1,474,497 | 11/1923 | Stolper . |
| 2,362,957 | 11/1944 | Hackett . |
| 2,427,128 | 4/1947 | Ettinger . |
| 2,695,607 | 11/1954 | Hipps et al. . |
| 2,863,444 | 7/1958 | Winsten . |
| 3,565,061 | 2/1971 | Reynolds . |
| 3,731,673 | 5/1973 | Halloran . |
| 3,750,652 | 8/1973 | Sherwin . |
| 3,776,240 | 12/1973 | Woodson . |
| 3,801,989 | 4/1974 | McKee . |
| 3,955,568 | 5/1976 | Neufeld . |
| 4,187,840 | 2/1980 | Watanabe . |
| 4,190,042 | 2/1980 | Sinnreich . |
| 4,259,068 | 3/1981 | Stephens . |
| 4,355,631 | 10/1982 | LeVahn . |
| 4,481,947 | 11/1984 | Chester . |
| 4,501,266 | 2/1985 | McDaniel . |
| 4,520,797 | 6/1985 | Peterson . |
| 4,567,885 | 2/1986 | Androphy . |
| 4,621,619 | 11/1986 | Sharpe . |
| 4,686,972 | 8/1987 | Kurland . |
| 4,726,356 | 2/1988 | Santilli et al. . |
| 4,738,248 | 4/1988 | Ray . |
| 4,747,395 | 5/1988 | Brief . |
| 4,945,897 | 8/1990 | Greenstein . |
| 4,993,875 | 2/1991 | Coes . |
| 5,002,547 | 3/1991 | Poggie et al. . |
| 5,035,700 | 7/1991 | Kenna . |
| 5,122,144 | 6/1992 | Bert et al. . |
| 5,190,549 | 3/1993 | Miller et al. . |

FOREIGN PATENT DOCUMENTS

| | | |
|---|---|---|
| 462077 | 9/1913 | France . |
| 1487486 | 7/1967 | France . |
| 2808970 | 9/1979 | Germany ..................... 606/86 |
| 300187 | 7/1981 | Germany . |
| 215468 | 11/1984 | Germany . |
| 1274432 | 5/1972 | United Kingdom . |
| 14918 | 4/1987 | United Kingdom ..................... D7/. |
| 634740 | 11/1978 | U.S.S.R. . |
| 1595499 | 9/1990 | U.S.S.R. . |

OTHER PUBLICATIONS

Brochure for "Eftekhar II Knee Prosthesis", in Class 606/88, undated.
Brochure of Innomed, Inc., Mentone, Ind., copyrighted 1989 entitled "Mark II Chandler Retractor".
Brochure for DePuy "New Jersey Tri-Compartmental Total Knee System", 1984 DuPuy, Inc.
Stille (1939) Catalog of Stainless Steel Retractors.
D. H. Levinthal, Journal of Bone & Joint Surgery (1931) "Knee Joint Retractors For Resections and Arthroplasties", pp. 378, 379.
Zimmer Inc. Catalog (1966), pp. 116, 117 and A163.

*Primary Examiner*—Corrine Maglione
*Attorney, Agent, or Firm*—Emch, Schaffer, Schaub & Porcello Co.

[57] ABSTRACT

A method of performing knee surgery and retractors and a femoral distractor for use in performing such method are provided, said retractors including a PCL tibial retractor, lateral patellar retractor, collateral ligament retractor, posterior cruciate ligament retractor and unicompartmental retractor designed to cooperate with one another in performing such method.

3 Claims, 10 Drawing Sheets

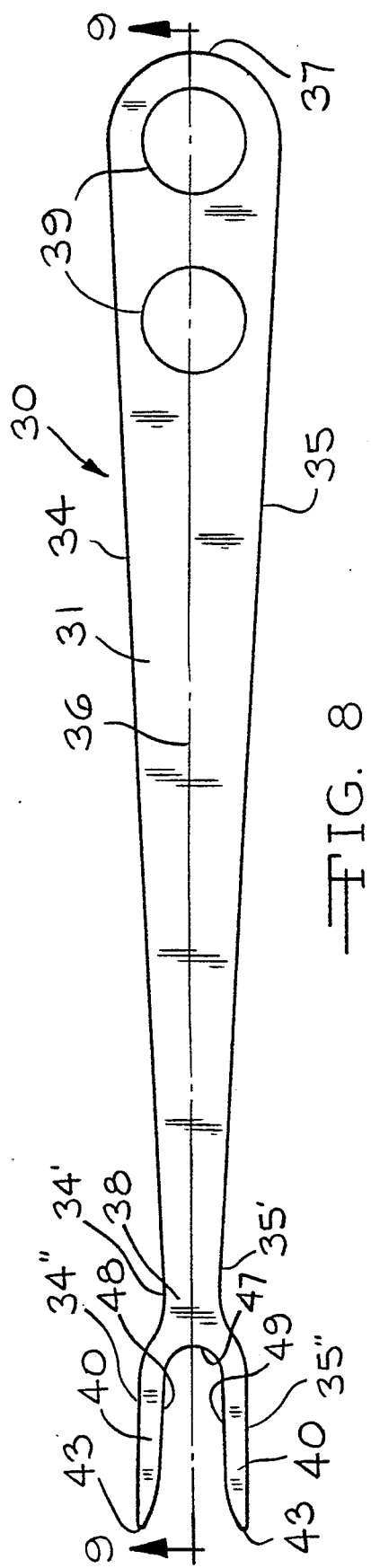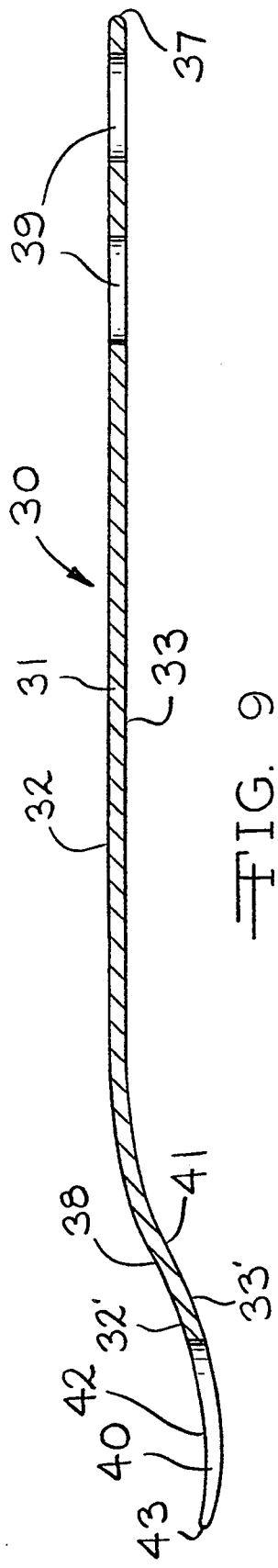

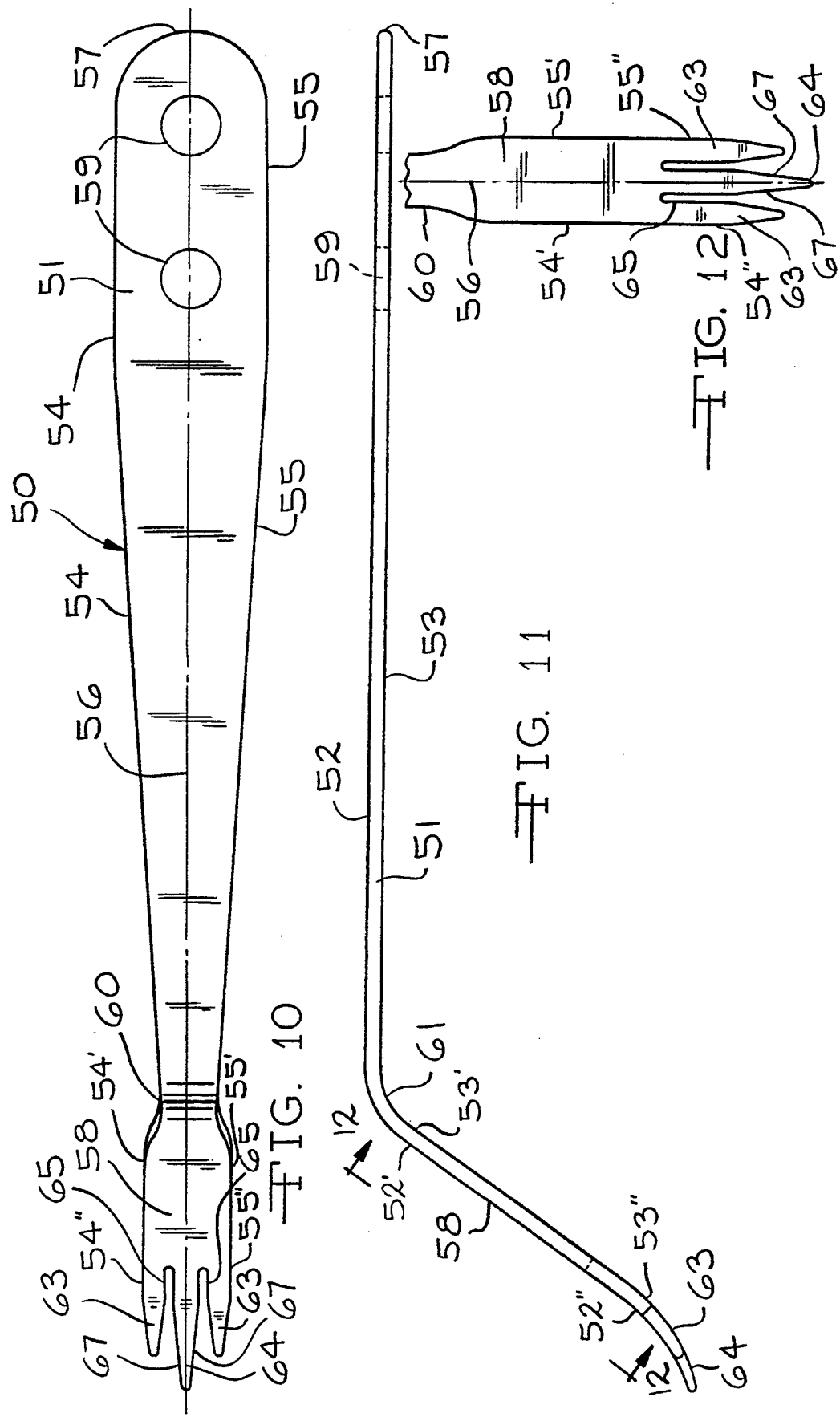

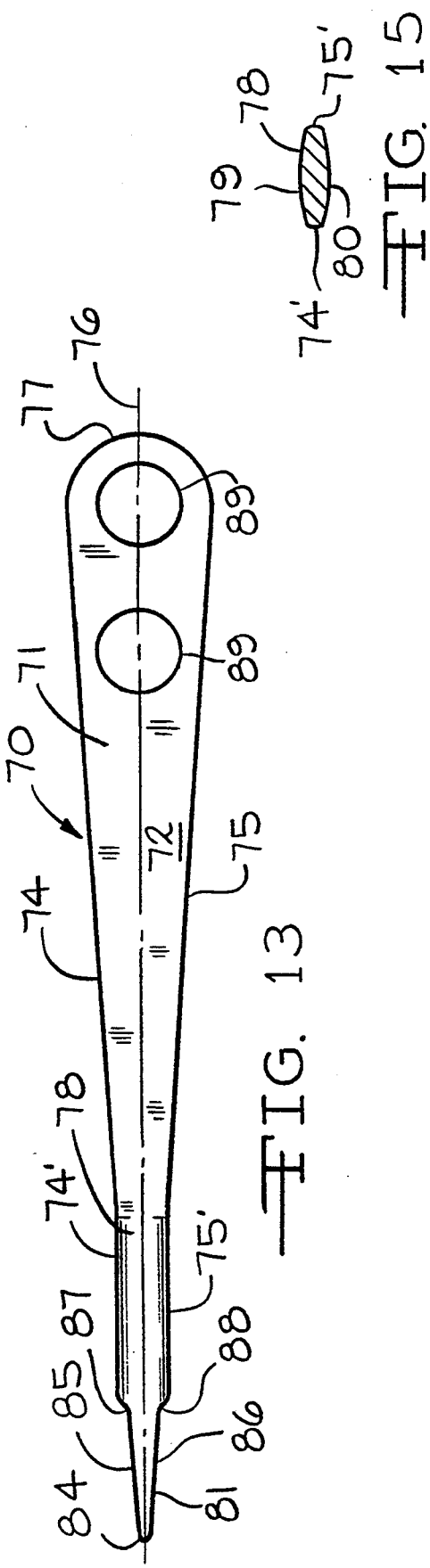
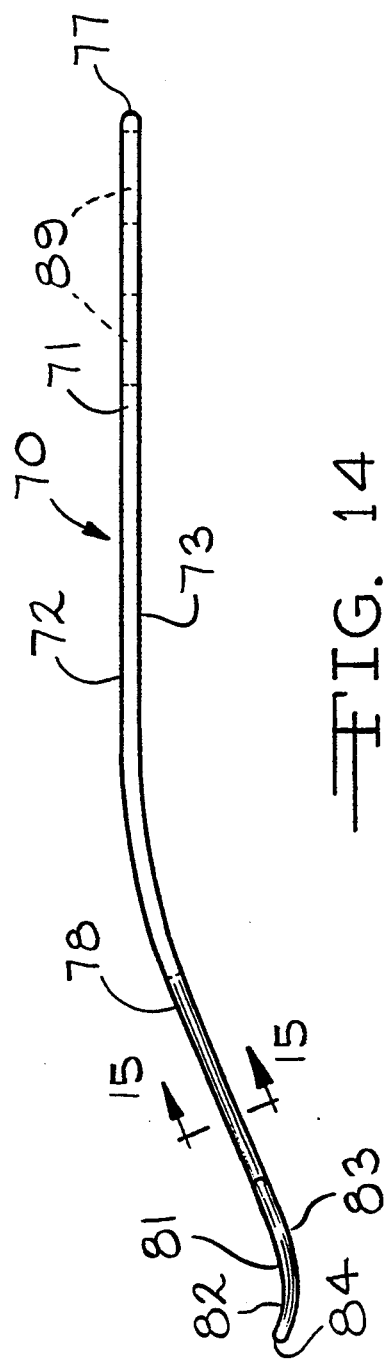

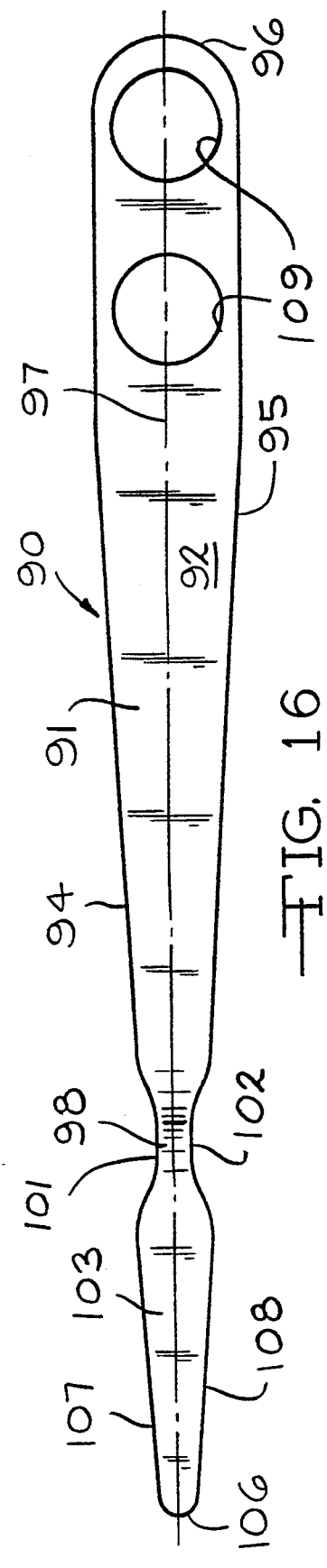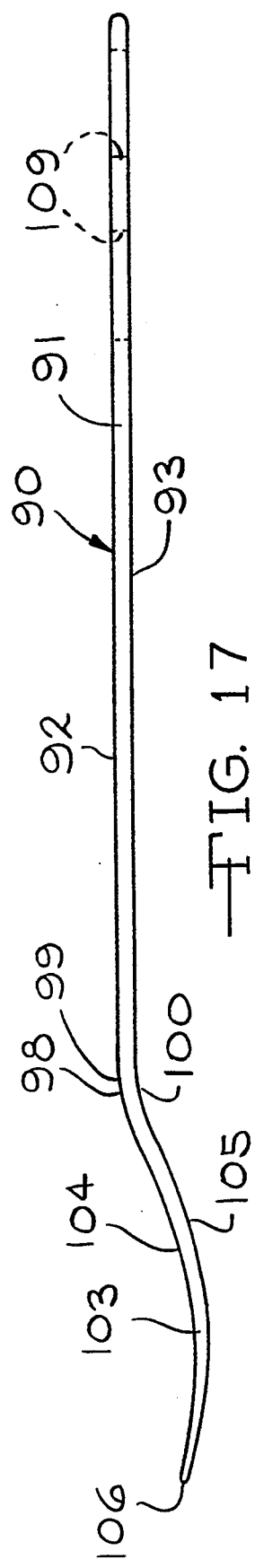

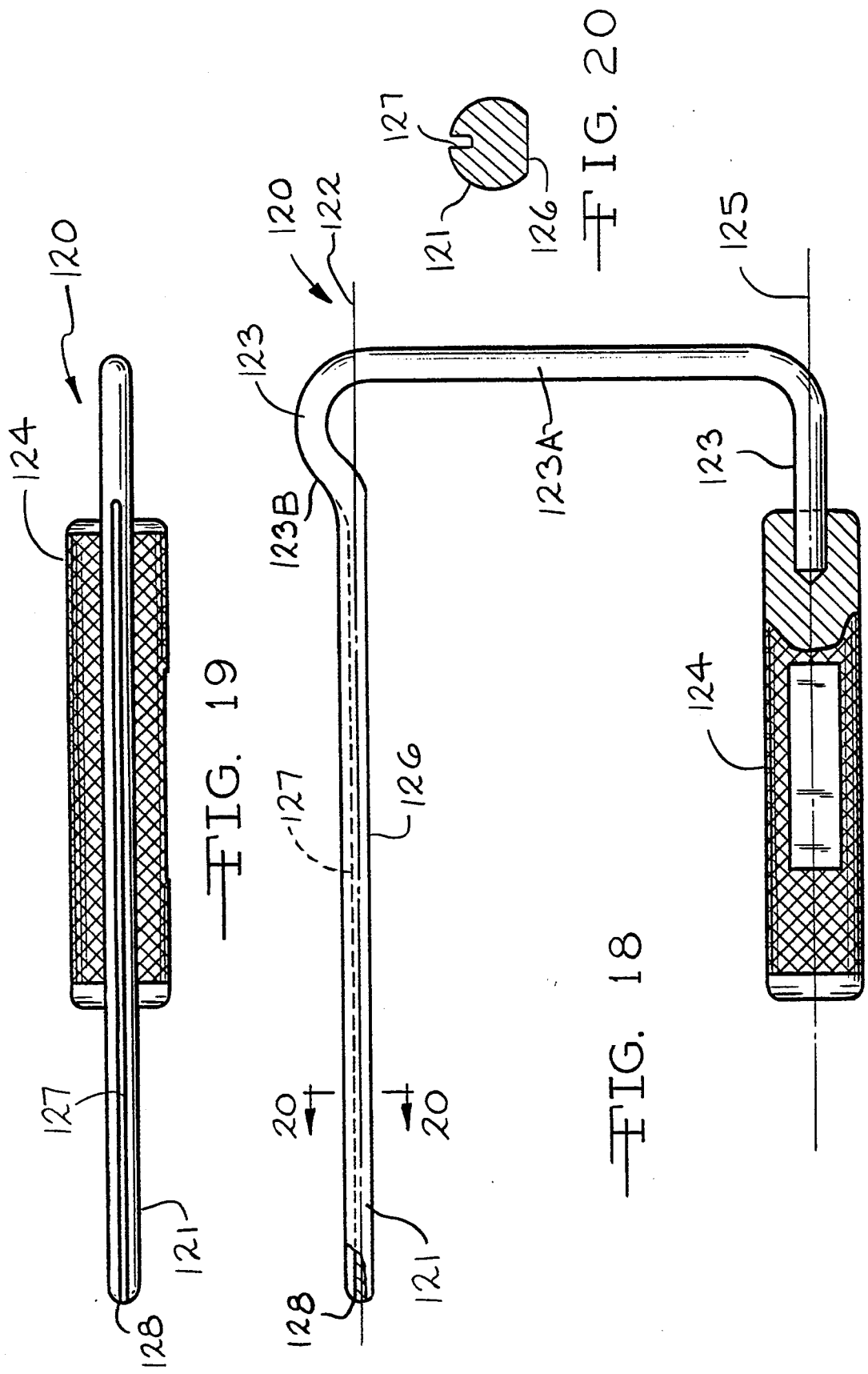

POSTERIOR CRUCIATE LIGAMENT RETRACTOR FOR USE IN PERFORMING KNEE SURGERY

This is a divisional of copending application(s) Ser. No. 07/988,205 filed on Dec. 9, 1992 now U.S. Pat. No. 5,334,194 which is a division of Ser. No. 07/508,090 filed Apr. 11, 1990 now U.S. Pat. No. 5,217,463.

BACKGROUND OF THE INVENTION

In performing knee surgery it is of the utmost importance to avoid or at least minimize damage to ligaments, tendons, muscles, nerves and other portions of the soft tissue while gaining access to and performing surgical procedures on various portions of bone structure of the knee. Heretofore, the retractors utilized in performing knee surgery have not been specifically tailored to permit maximum access to the bone structure intended for osteotomy procedures while at the same time providing maximum protection for various soft tissue members.

U.S. Pat. No. 4,820,797 discloses a collateral ligament retractor for use in knee surgery. Such retractor includes a member having a cupped arcuate finger for insertion into the knee joint along and partly around the tibial plateau and a curved portion extending from the finger outwardly around the ligament, then extending back substantially in the same direction as the finger and including a downwardly extending pivoted elongated arm extending to a position behind the knee above the calf. A second member of similar design but larger to accomodate the everted patella is positioned around the opposite ligament and a tension member such as a coil spring is connected to the outer end of the arms of the members for biasing them toward one another to hold the ligaments in a retracted position.

Patentschrift No. DD-215-46S-A of the Duetsche Demokratische Republic discloses a wound retractor for knee surgery which has a holder having a hook-shaped convex blade at tile distal end.

U.S. Pat. No. 2,695,607 discloses a surgical retractor intended to hold back flesh and muscles from a bone on which surgical treatment is to be performed.

Zimmer Company, Warsaw, Indiana, Catalog for 1966 discloses on page 117 a Blount Knee Retractor having a handle with a tip disposed at an angle of more than 90° which is intended to be inserted into the knee joint just proximal to the cartilage so as to expose the line of disection while broadening out to retract the superficial soft tissue without use of an additional retractor.

None of the retractors disclosed in the above referenced prior art or any other retractors known to the applicant have the capability of providing the degree of protection as those of the present invention and no prior art surgical procedures for knee surgery are as effective in permitting access to the bone structure upon which osteotomy procedures are to be performed while providing protection to the critical soft tissue.

SUMMARY OF THE INVENTION

The present invention relates to a method of performing knee surgery and to retractors and a femoral distractor for use in performing such surgery.

BRIEF DESCRIPTION OF THE DRAWINGS

FIG. 8 is a top plan view of the PCL tibial retractor.

FIG. 9 is a sectional view taken along line 9—9 of FIG. 8.

FIG. 10 is a top plan view of the lateral patellar retractor of the present invention.

FIG. 11 is an elevational view of the lateral patellar retractor as shown in FIG. 10.

FIG. 12 is a fragmentary plan view of the retracting end of the lateral patellar retractor shown in FIG. 10 with such end rotated for clarity.

FIG. 13 is a top plan view of the posterior cruciate ligament retractor of the present invention.

FIG. 14 is a side elevational view of the posterior cruciate ligament retractor as shown in FIG. 13.

FIG. 15 is a sectional view taken through line 15—15 of FIG. 14.

FIG. 16 is a top plan view of the collateral ligament retractor of the present invention.

FIG. 17 is an elevational view of the collateral ligament retractor as shown in FIG. 16.

FIG. 18 is a top plan view, partly in section, of the femoral distractor of the present invention.

FIG. 19 is an elevational view of the femoral distractor as shown in FIG. 18.

FIG. 20 is a sectional view taken through line 20-20 of FIG. 18.

DETAILED DESCRIPTION OF THE INVENTION

Figure 1:
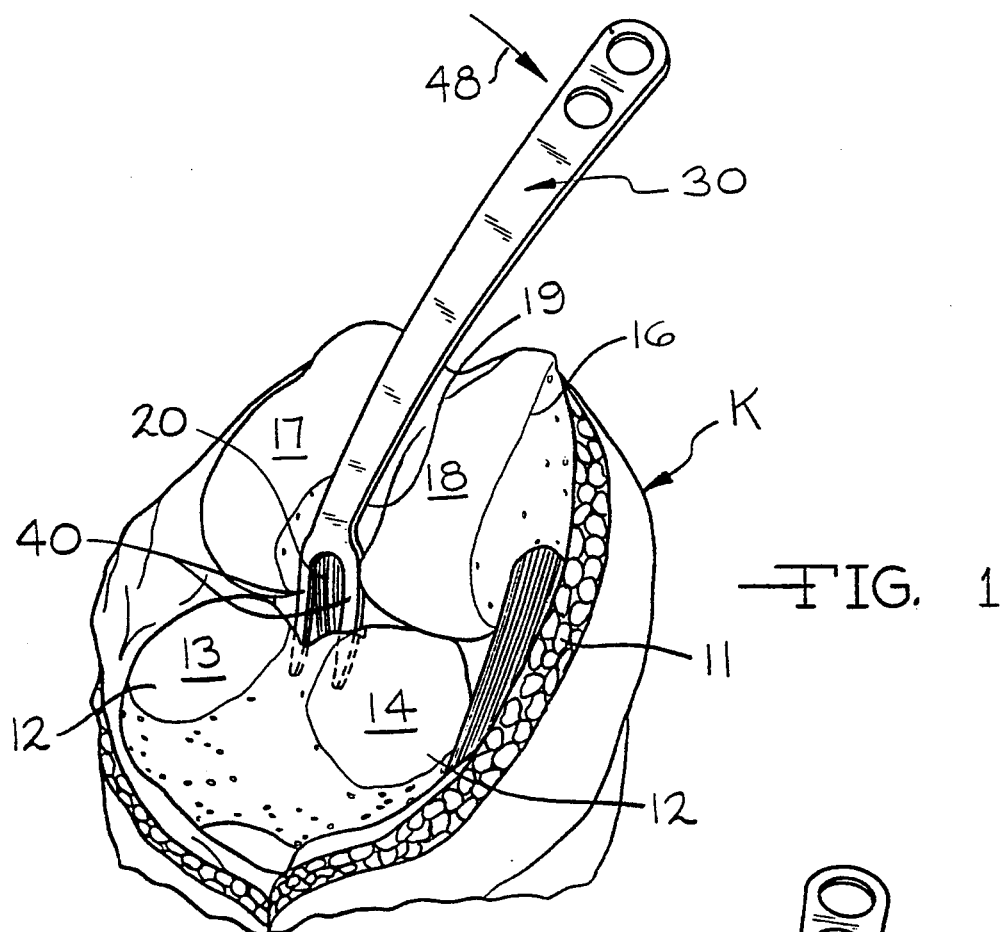
FIG. 1 is a perspective view showing a step in the knee surgery showing use of the PCL tibial retractor of the present invention.

Referring to FIGS. 1-7, there is shown a knee generally designated by the letter K in which an incision has been made through the skin and flesh 11 to expose the interior members upon which osteotomy and other procedures are to be performed. Such other procedures may include fitment and placement of an artificial knee prosthesis. Once such prosthesis is shown and described in the brochure published by Johnson & Johnson Orthopaedics, New Brunswick, N.J., in September 1988 entitled "P. F. C. TOTAL KNEE SYSTEM" ("P.F.C." is a registered trademark of Johnson & Johnson Orthopaedies Inc.) using a surgical technique desribed in a booklet published by Johnson & Johnson Products Inc. entitled "Surgical Technique - The Press Fit Condylar Total Knee System With Specialist Instrument". Although retractors will obviously be used throughout the entire surgical procedure of implanting any such prosthesis, the retractors and method defined by the present invention are directed primarily to preparation of various portions of the bone structure for receiving any such prosthesis and protection of the ligaments, tendons, muscles, nerves and other critical soft tissue members during osteotomy and other procedures.

As shown in FIGS. 1–7, the incision in the knee. K permits access to the tibial plateau 12 including lateral and medial tibial condyles 13 and 14, respectively. With knee bent as shown in FIGS. 1–7 there is also exposed the distal femur 16 including lateral and medial femoral condyles 17 and 18, respectively. The intercondylar notch (femoral trochlear groove) 19 separates the lateral and medial femoral condyles 17 and 18, respectively. The posterior cruciate ligament 20 is attached to the femur and tibia proximally and distally, respectively, and needs to be completely protected during the osteotomy.

Figure 2:
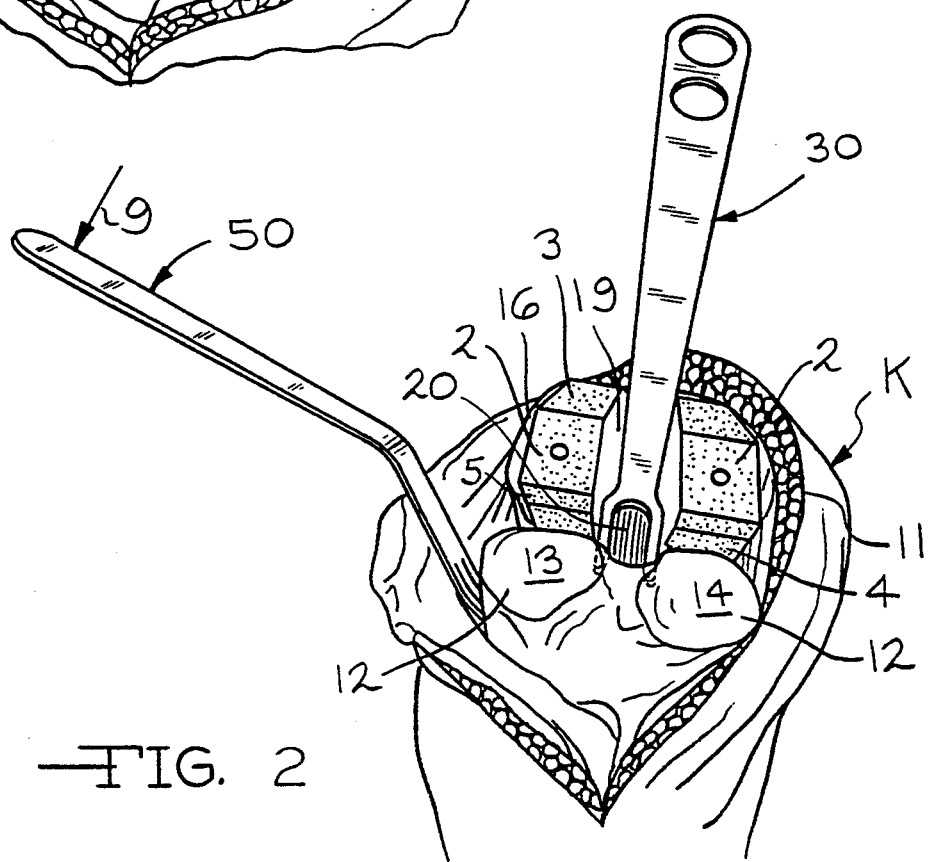
FIG. 2 is a perspective view similar to FIG. 1 showing the PCL tibial retractor and the lateral patellar retractor of the present invention in use during surgery.
Figure 3:
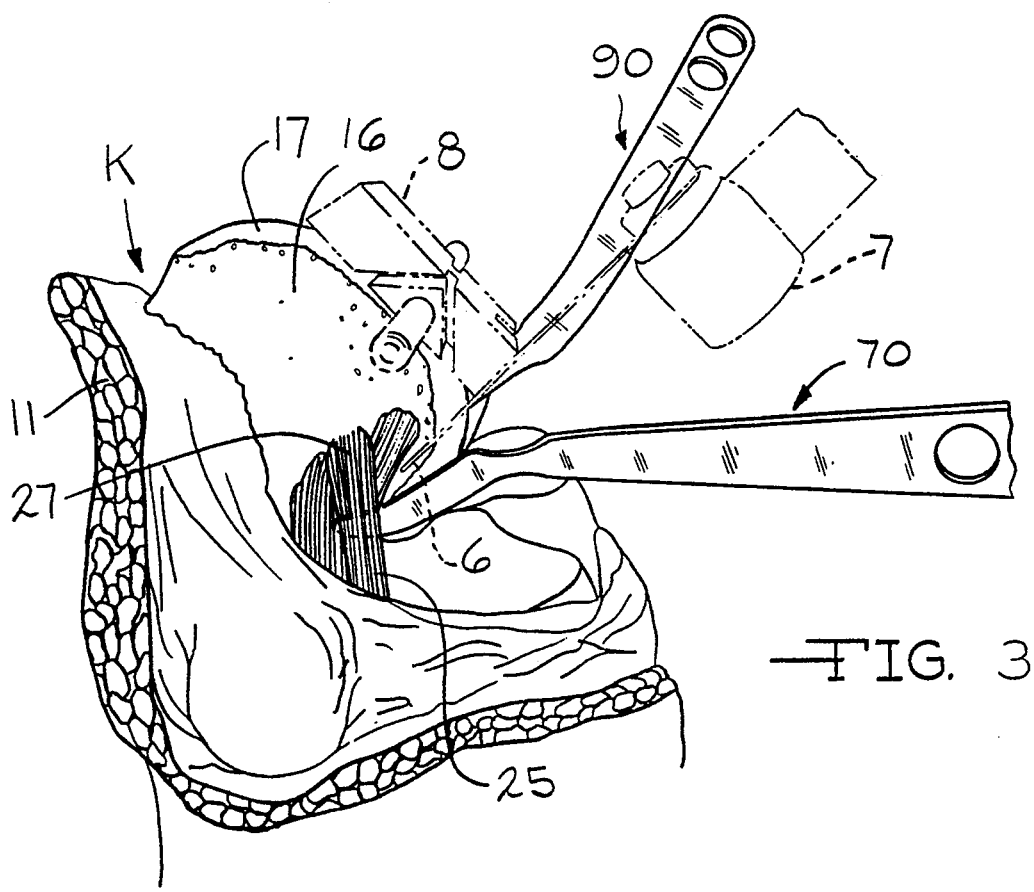
FIG. 3 is a perspective view looking from the side of a knee during surgery and showing the step of using a posterior cruciate ligament retractor and a collateral ligament retractor according to the present invention.
Figure 4:
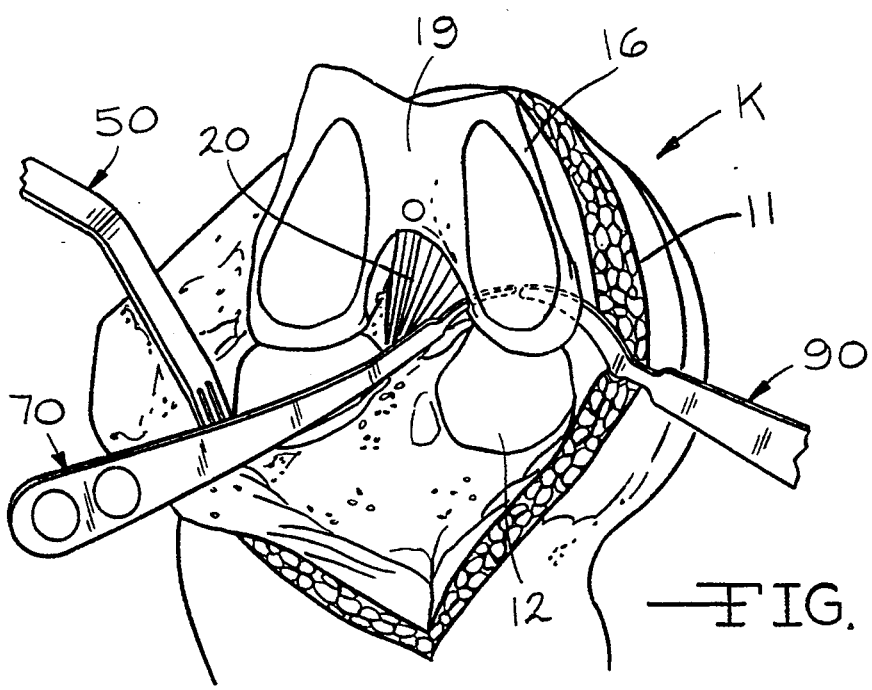
FIG. 4 is a perspective view taken from the front of a knee during surgery showing the step of using the lateral patellar retractor, the posterior cruciate ligament retractor and the collateral ligament retractor.
Figure 5:
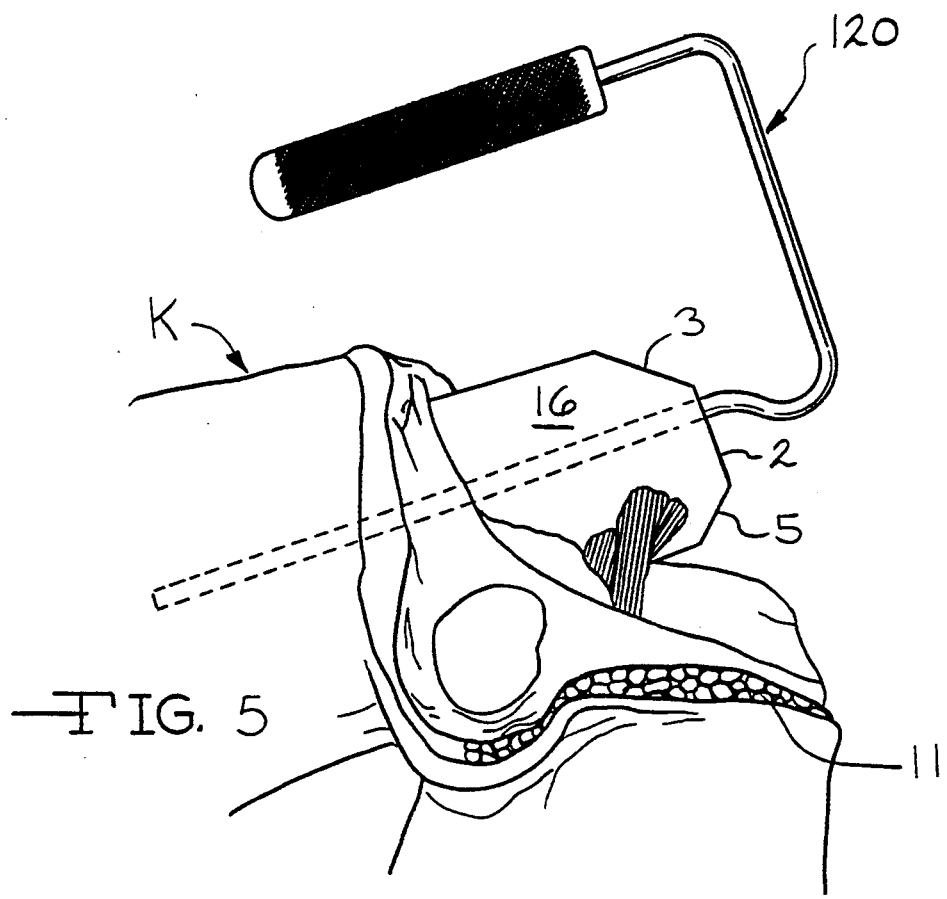
FIGS. 5 and 6 are perspective views from different angles showing the use of the femoral distractor portion of the present invention.
Figure 6:
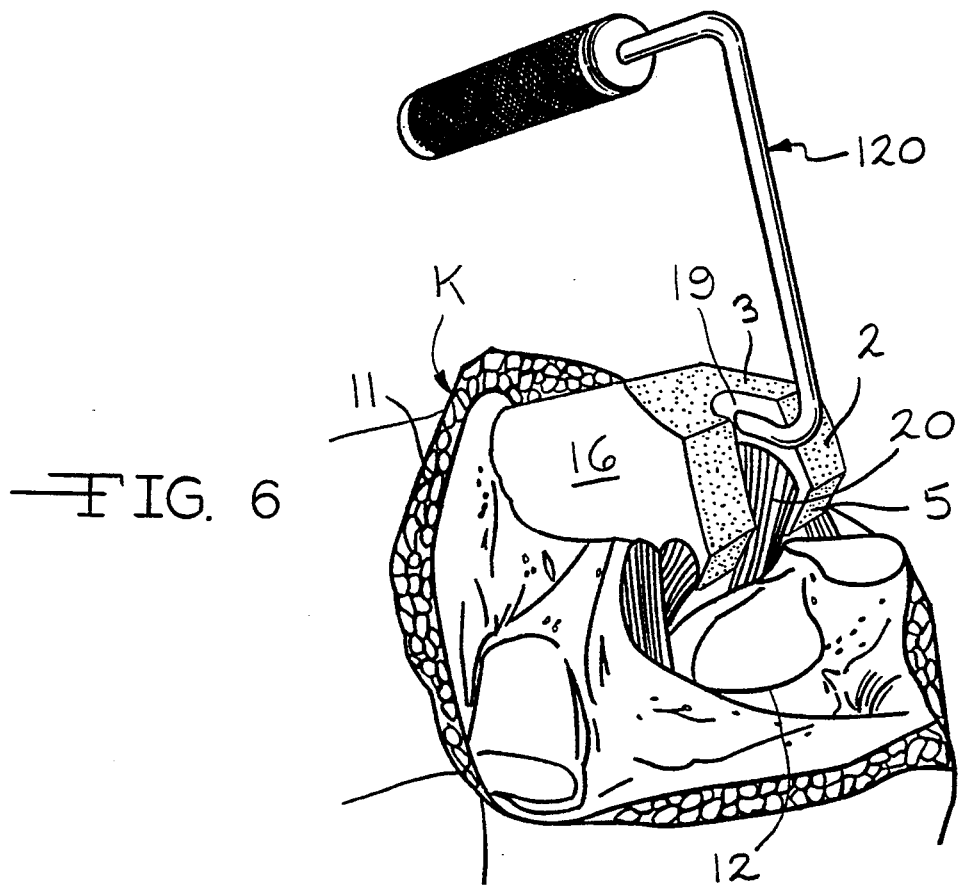
Figure 7:
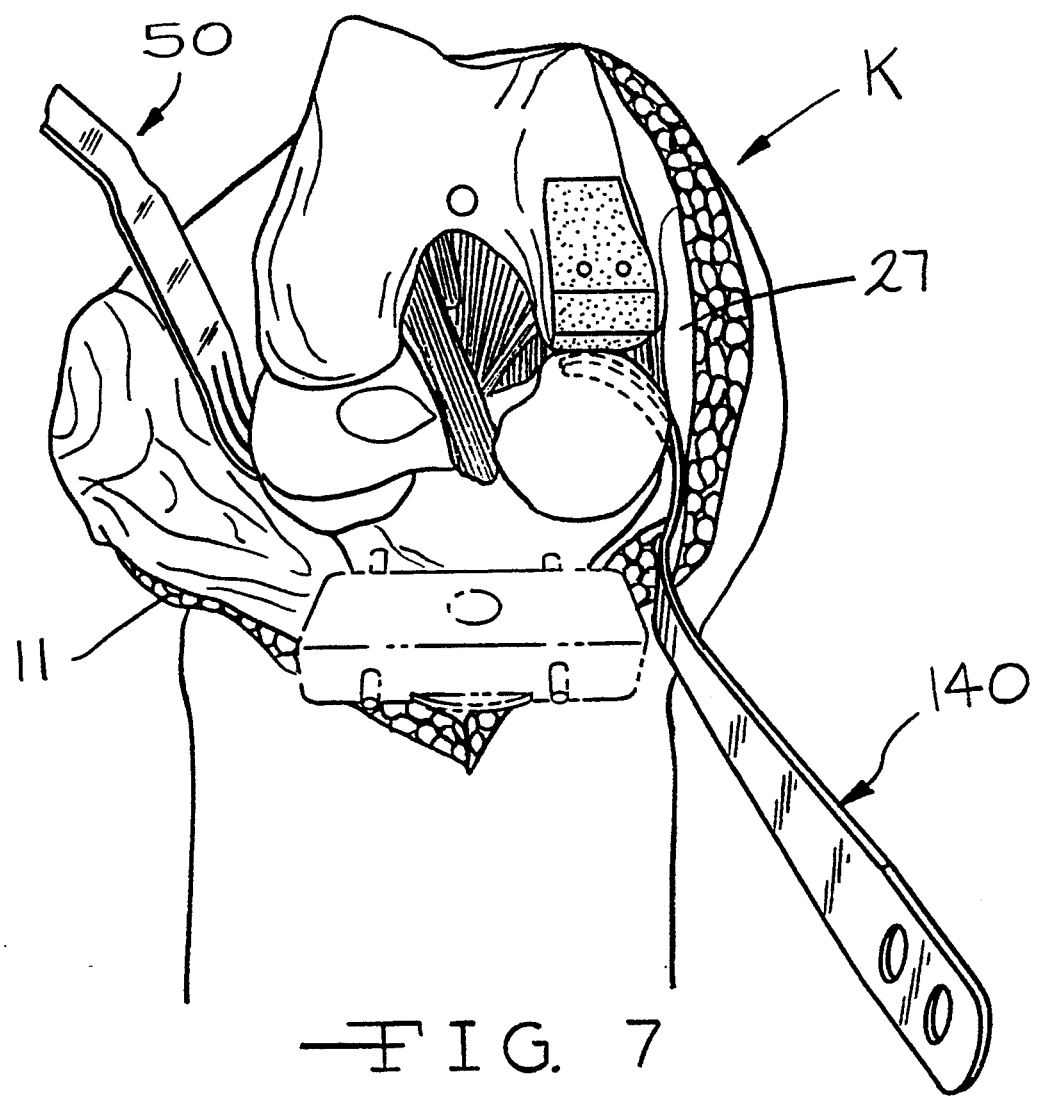
FIG. 7 is a perspective view taken from the front showing the step of using unicompartmental retractor in Combination with the lateral patellar retractor.

FIGS. 2, 5 and 6 show the distal femur 16 following condylar osteotomies including distal femoral 2, anterior 3, posterior 4 and chamfer 5 cuts while FIG. 3 shows the position of the blade 6 of an oscillating saw 7, cutting guide 8 and PCL and collateral ligament retractors to be described hereinafter during posterior 4 femoral osteotomy. Also shown in FIG. 3 is the fibular (lateral collateral) ligament 25 which extends from the lateral aspect 27 of the lateral femoral condyle 17 to the head of the fibula (not shown). Additionally, as shown in FIG. 7, the collateral ligament 27, including its surrounding capsule is also exposed and needs to be protected during unilateral proximal tibial osteotomy.

Referring now to FIGS. 1, 2, 8 and 9, there is provided a PCL tibial retractor 30 which will be described as manufactured and as used in the surgical method herein. The PCL tibial retractor 30 includes a handle 31 which has generally flat upper and lower parallel surfaces 32 and 33, respectively, and edges 34 and 35 which taper inwardly toward each other and toward a longitudinal axis 36 from an area of maximum breadth adjacent an arcuate free end 37. The handle 31 may have one or more holes 39 to provide a place for hooking a weight thereto.

Integrally formed with the handle 31 is an integral support section 38 from which extend a pair of integral prongs 40. The support section 38 and prongs 40 will be described with the handle 31 oriented in a horizontal position. With the handle 31 so positioned, the support section 38 and prongs 40 will have an upper surface 32' and a lower surface 33' following a gentle S-shaped curve such that the support section 38 follows a curve 41 downwardly from horizontal and the prongs 40 follow a reverse curve 42 having a radius of curvature substantially the same as that of the support section and extending to ends 43 which are angled upwardly toward such horizontal plane at an angle of about 5° +/−2°. The lower surface 33' of the curved portion 41 has a radius of curvature of 3.312 inches +/−0.5 inch with its center located 3.312 inches below the lower surface 33 of the handle 31 and 3.312 inches behind the ends 43. The upper surface 32' of the curved portion 42 has a radius of curvature of 3.312 inches +/−0.5 inch with its center located 2.625 inches above tile upper surface 32 of the handle 31 and 0.400 inch behind the ends 43. If desired, there could be a short planar segment separating the curved portion 41 from the reverse curve 42. The PCL tibial retractor as shown in FIG. 9 has a uniform thickness of 0.120 inch throughout except for the last 0.5 inch of the prongs 40 adjacent the ends 43 each of which tapers to a thickness of 0.030 inch +/−0.010 inch at the ends 43. The thickness and shape of the handle are not critical; however, the handle must be sufficiently rigid to prevent excessive bending during use and must have a shape which is convenient to use without obstructing desired surgical procedures when in use.

Referring now to FIG. 8, the support section 38 includes edges 34' and 35' which taper inwardly toward a vertical plane lying on the longitudinal axis 36 to a point of minimum breadth just before tile juncture between the support section 38 and the prongs 40. This area should have a breadth of 0.430 inch +/−0.020 inch in order that it can fit within the intercondylar notch 19 of the femurs and to use that portion as a fulcrum without damaging it. If desired, the support section 38 could have parallel edges 34' and 35' spaced apart such distance, in which case, such edges would flare outwardly at their respective junctures with the handle 31.

As can also be seen in FIG. 8, the edges 34' and 35' join with the outer edges 34" and 35", respectively, of the prongs 40. Such outer edges 34" and 35" follow a straight-line path parallel to such vertical plane lying on the longitudinal axis 36 and are spaced apart 0.770 inch +/−0.020 inch.

The prongs 40 have inner edges 48 and 49 which follow a straight line path in the area of juncture with said integral support section 38 and which taper outwardly from said vertical plane at an angle of 5° for the 0.5 inch portion adjacent the respective ends 43. The distance between the inner edges 48 and 49 in the straight line portion of the prongs is 0.430 inch +/−0.020 inch. The ends 43 are rounded with the respective tips having a breadth of 0.030 inch +/−0.010 inch. The inner edges 48 and 49 are joined by an arcuate segment 47, preferably having a radius of at least 0.215 inch.

As can be seen in FIGS. 1 and 2, the size, shape and space between the prongs 40 permit the prongs to straddle and thus protect the posterior cruciate ligament 20 and for the portions adjacent the ends 43 to rest against the posterior side of the respective lateral tibial condyle 13 and medial tibial condyle 14. The PCL tibial retractor 30 may then be moved in a direction toward the patient as indicated by the arrow 48 thus using the intercondylar notch 19 as a fulcrum. Such positioning presents the surfaces of the lateral tibial condyle 13 and medial tibial condyle 14 for osteotomy.

Referring now to FIGS. 2, 10, 11 and 12, there is shown a lateral patellar retractor 50 which includes a handle 51 having a longitudinal axis 56 and having generally flat upper and lower parallel surfaces 52 and 53, respectively, and edges 54 and 55. As may be seen in FIG. 10, the edges 54 and 55 are parallel to one another and to the longitudinal axis 56 in the area extending to an arcuate free end 57. The handle has one or more apetures 59 through which weighted hooks may be placed if it is desired to retain the retractor in position without a person attending thereto. Integrally formed with the handle 51 is a flat planar support section 58 which is disposed at an angle downwardly of approximately 55° from horizontal when the handle 51 is oriented in a horizontal position. Such angle could vary by as much as +/−30°. An arcuate section 61 joins the support section 58 to the handle 51.

Approximately one-third of the way between the free end 57 and the arcuate section 61, the edges 54 and 55 taper inwardly toward the longitudinal axis 56 at an angle of approximately 4°. The edges 54 and 55 continue to taper inwardly toward such longitudinal axis until they reach a point of minimum breadth 60. As can be seen in FIGS. 10 and 12, the support section 58 has edges 54' and 55' which are parallel, to each other and to a vertical plane lying on the longitudinal axis. Preferably the distance between such edges is about 0.71 inch; however, since its function is primarily to move the incised soft tissue away from the lateral tibial condyle 13 (see FIG. 2), it could be broader or somewhat narrower and the edges 54' and 55' are not required to be straight.

Integrally formed with and extending from the support section 58 are three prongs including a pair of side prongs 63 and a center prong 64. As can be seen from the drawings, the center prong 64 extends beyond the ends of the two side prongs 63. The prongs 63 and 64 are joined to the planar portion of the support section 58 and, as may be seen in FIG. 11 have upper and lower surfaces 52" and 53" which initially follow a straight line path and terminate in an arcuate path. The arcuate path has a radius of 1.62 inch +/−0.5 inch to the upper surface 52" with a center located 1.19 inch below the plane defined by the upper surface 52 of the handle 51 and 0.54 inch beyond the end of the center prong 64. The segment of the prongs 63 and 64 following a straight line path is approximately 0.35 inch while the overall length of the side prongs 63 including the portion with the straight line segment is 1.07 inch +/−0.020 inch while the overall length of the center prong 64 is 1.32 inch +/−0.020 inch. Thus, the center prong 64 extends beyond the prongs 63 by 0.25 inch.

The side prongs 63 have outer edges 54" and 55" each of which, for about 0.35 inch, are extensions of and lie in the same path followed by the edges 54" and 55', respectively, of the adjacent portion of the support section 58. Each of the side prongs 63 has an inner edge 65 which, for about 0.35 inch, is parallel to the vertical plane extending through the longitudinal axis 56. The center prong 64 has a pair of edges 67, each of which, for about 0.35 inch, is spaced from and parallel to the first portion of the inner edges 65.

The end portions of each of the prongs 63 and 64 taper to rounded tips having a radius of 0.03 inch +/−0.010 inch in both the horizontal and vertical planes. Thus, as can be seen in FIG. 12, the edges 54" and 65; and 55" and 65 of each of the side prongs 63, for a distance of approximately 0.72 inch from their respective ends are disposed at an angle of approximately 16° to each other. Similarly, the edges 67 of the center prong 64 for a distance of approximately 0.97 inch from its end are disposed at an angle of approximately 16° to each other.

The distance between the outer edges 54" and 55" of the side prongs 63 is 0.71 inch +/−0.020 inch in the area parallel to the vertical plane extending through the longitudinal axis 56 with each of such prongs having a breadth in that area of 0.18 inch. The breadth of the center prong 64 in that area in which the edges 67 are parallel is 0.20 inch.

The thickness of the lateral patellar retractor 50 is 0.12 inches throughout the entire length except for the prongs 63 and 64 which taper at their ends to a thickness of 0.06 inch +/−0.010 inch. The taper in thickness for the side prongs 63 and center prong 64 begins at a point 0.35 inch from their respective junctures with the support section 58 as determined by the ends of the slots between the prongs. If desired, the lateral patellar retractor 50 could have four prongs with tile two center prongs extending beyond the ends of the two side prongs.

As can be seen in FIG. 2, such construction permits the lateral patellar retractor 50 to be readily inserted along side of the lateral tibial condyle 13 so that the retractor 50 may use the shelve of such lateral tibial condyle 13 as its restive point. In as much as the center prong 64 is longer than tile side prongs 63, the insertion may be easily accomplished. Such elongated center prong coupled with the curved upper and lower surfaces 52 and 53 at the ends of such center prong 64 and side prong 63 permit the lateral patellar retractor 50 to slide around the lateral tibial condyle with minimum damage to the surrounding soft tissue. In particular, such configuration clearly avoids damage to the common peroneal nerve, the tibial condyle itself or the attendant lateral soft tissue structures. The broad flat support section 58 engages the lateral soft tissue structure as the handle is moved in the direction indicated by the arrow 9. Thus, when the lateral patellar retractor 50 is in such position and the PCL tibial retractor 30 is positioned as described in FIG. 1 and as shown in FIG. 2, there is provided an unimpeded presentation of the tibial plateau 12 including the lateral tibial condyle 13 and medial tibial condyle 14 with the prepared distal femoral surface 16 held safely clear of the field to allow accurate tibial osteotomy.

Referring now to FIGS. 3, 4 and 13–17, there is shown a posterior cruciate ligament retractor 70 and collateral ligament retractor 90. The posterior cruciate ligament retractor 70 includes a handle 71 which has generally flat upper and lower parallel surfaces 72 and 73, respectively, and edges 74 and 75 which taper inwardly toward the each other and toward a longitudinal axis 76 from an area of maximum breadth adjacent an arcuate free end 77. The handle 71 may have one or more holes 89 to provide a place for hooking a weight thereto. The handle 71 merges into an integral support section 78 having edges 74' and 75'. The edges 74' and 75' are parallel to a vertical plane passing through the longitudinal axis 76 assuming that the portion of the handle 71 in the area of the free end 77 is in a horizontal position.

As can be seen from FIG. 15, the support section 78 has upper and lower surfaces 79 and 80, respectively, each of which has an arcuate configuration extending from edge 74' to edge 75'. Such arcuate configuration is not critical and one or both of such surfaces 79 and 80 could be fiat. The distance between the edges 74' and 75' of the integral support section 78 is 0.43 inch +/−0.020 inch and the thickness in the center of such support section 78 and the handle 71 is about 0.12 inch. The thickness and shape of the handle 71 and support section 78 are not critical; however, they must be sufficiently rigid to prevent excessive bending during use and must have a shape which functions to retract and protect the appropriate soft tissue without obstructing desired surgical procedures when in use.

The handle 71 curves downwardly in an arcuate path with the lower surface 73 extending through an arc of 22° with a radius of 5.0 inch +/−0.5 inch. The integral support section 78 extends in a generally straight line path downwardly at an angle of 22° +/−1.5° from horizontal.

A tip 81 is integrally formed with and extends from the integral support section 78 to an end 84. The tip 81 has upper and lower surfaces 82 and 83 which follow an arcuate path reversed from the arcuate path of the handle 71 with the upper surface 82 having a radius of 2.0 inch +/−0.4 inch with a center of radius located 0.78 inch above a plane defined by the upper surface 72 of the handle 71 and approximately 0.18 inch behind the end 84 of the tip 81. The length of the tip 81 from the support section 78 to the end 84 is 1.10 inch +/−0.020 inch. The end 84 and the portion of the tip 81 adjacent thereto are angled upwardly toward horizontal. The tip 81 has edges 85 and 86 which taper at an angle of 4° +/−1° to a vertical plane passing through the longitudinal axis (included angle equals 8° +/−2°). Each of the edges 85 and 86 flares outwardly through arcuate sections 87 and 88, respectively, in the area where the tip 81 merges with the support section 78. The edges 85 and 86 extend to the end 84 which is defined by an arcuate path having a radius of 0.05 inch +/−0.01 inch.

The thickness of the tip 81 tapers from 0.12 inch at the support section 78 to 0.045 inch +/−0.010 inch at the end 84. The end is rounded from the lower surface 83 to the upper surface 82 with a radius of 0.04 inch +/−0.01 inch.

Referring now to FIGS. 16 and 17, the collateral ligament retractor 90 includes a handle 91 which has generally flat upper and lower parallel surfaces 92 and 93, respectively, and edges 94 and 95. The edges 94 and 95 are generally parallel in the area adjacent an arcuate free end 96. The handle 91 may have one or more holes 109 to provide a place for hooking weights thereto. At any desired point, the edges 94 and 95 taper toward a longitudinal axis 97. The handle 91 merges into an integral support section 98. The integral support section 98 includes upper and lower surfaces 99 and 100, respectively, which curve downwardly following a curved path through an arc of approximately 28° on a radius of approximately 1.25 inches from the lower surface 100. The support section 98 has edges 101 and 102 which follow a straight line path parallel to a vertical plane passing through the longitudinal axis 97 and flare outwardly where they are joined to edges 94 and 95, respectively, of the handle 91. The breadth of the support section 98 in the area in which the edges 101 and 102 follow a straight line path is 0.24 inch +/−0.020 inch.

A tip 103 extends from the integral support section 98 to a blunt free end 106. The tip 103 has upper and lower surfaces 104 and 105, respectively, which follow a curved path through an arc of 44.5°+/−0.5° and having a radius of 3.0 inches, the center of which is 2.5 inches +/−0.5 inch above a horizontal plane defined by the upper surface 92 of the handle and positioned 0.88 inch behind the end 106 of the tip 103. Thus, as can be seen, the tip 103 has its end 106 pointed slightly upwardly toward the horizontal plane defined by the upper surface 92; however, it does not extend up to such plane. At its lowest point, the tip 106 is approximately 0.59 inch below such horizontal plane.

The tip 103 has edges 107 and 108, respectively, which taper inwardly toward a vertical plane passing through tile longitudinal axis 97 at an angle of 4° +/−1° and joining the end 106 which has a radius of 0.125 inch +/−0.010 inch. Thus the included angle between the edges is 8° +/−2°. The tip 103 has a maximum breadth 0.41 inch +/−0.02 inch located 1.93 inch from the end 106. The breadth near tile end 106 at the point of juncture between the straight line segment of the edges 107 and 108 and the arcuate tip is 0.25 inch +/−0.02 inch.

The collateral ligament retractor 90 has a thickness of 0.12 inch throughout the handle portion 91 and the integral support section 98 and tapers to a thickness of 0.09 inch +/−0.02 inch at the end 106 with the end rounded in the vertical direction on a radius of 0.045 inch +/−0.01 inch. The thickness and shape of the handle 91 and the thickness of the support section 98 are not critical; however, they must be sufficiently rigid to prevent excessive bending when in use and must have a shape which functions to retract and protect the appropriate soft tissue without obstructing surgical procedures when in use.

Referring now to FIGS. 5, 6 and 18–20, there is shown a femoral distractor 120 for use in providing traction to the femur during surgery. Such distraction opens the joint to enhance visualization of the posterior capsule and facilitate removal of osteophytes, loose bodies and residual meniscal tissue. Such distraction also assists in accurate evaluation of the flexian gap. The femoral distractor 120 of the present invention permits the surgeon to provide maximum traction with minimized possibility of damage and ease of insertion into the medullary canal of the femur and includes vent means provided to relieve pressure during such insertion.

The femoral distractor 120 includes an insertion rod 121 following a straight line path along a longitudinal axis 122, a generally U-shaped support rod 123 integrally formed therewith and a handle 124 joined to support rod 123 along a second longitudinal axis 125 parallel to and spaced from the longitudinal axis 122.

The insertion rod 121 may have a circular cross-sectional configuration but preferably has a cross-sectional configuration such as that shown in FIG. 20, which can best be described as a circular cross-sectional configuration from which a chordal segment has been removed to provide a flat planar surface 126 in the area facing toward the handle 124.

The insertion rod 121 is also provided with a longitudinal groove 127 extending parallel lo the longitudinal axis 122 from a rounded free end 128 to the juncture of the insertion rod 121 with tile support rod 123. The groove 127 is positioned opposite the flat planar face 126 and provides a vent passageway to relieve pressure as the insertion rod is inserted into the medullary canal of the femur.

A significant feature of the femoral distractor 120 of the present invention resides in the configuration of the support rod 123 in the area of its juncture with the insertion rod 121. Thus, as shown most clearly in FIG. 18, a major portion 123A of the support rod 123 is disposed at an angle of 90° to the respective longitudinal axes 122 and 125. The portion forming the corner 123B initially follows an arcuate path in a direction away from both of said longitudinal axes 122 and 125 followed by a reverse curved portion joining it to the major portion 123A. Such construction permits the surgeon to apply the needed pressure required for maximum distraction under the circumstances while ensuring against undue pressure being placed against that portion of the femur adjacent the entry point of insertion into the medullary canal. Thus, construction of the support rod 123 with the outwardly bent corner 123B which initially extends away from the longitudinal axis 125 on which the handle is placed appears to provide for a more uniform distribution of the stresses over a large portion of the femur during distraction. In contrast, a distractor which follows a simple arcuate 90° path from the insertion rod to the support rod appears to concentrate excessive pressure at that portion of the femur immediately adjacent the point of insertion into the medullary canal. Such excessive pressure may also occur when distraction is performed by lifting the protruding end of a straight insertion rod which had been placed in the medullary canal.

Figure 21:
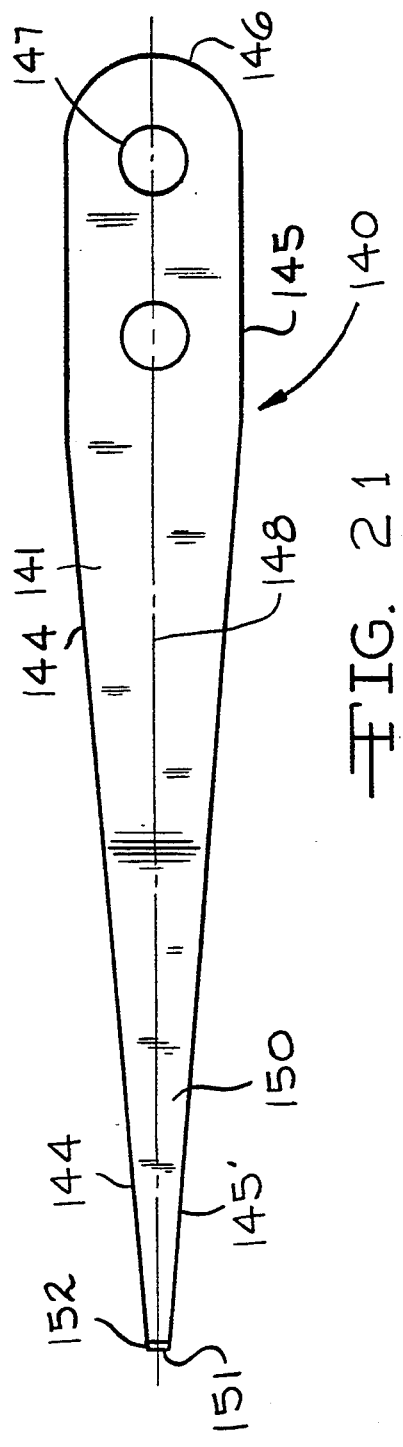
FIG. 21 is a top plan view of the unicompartmental retractor of the present invention.
Figure 22:
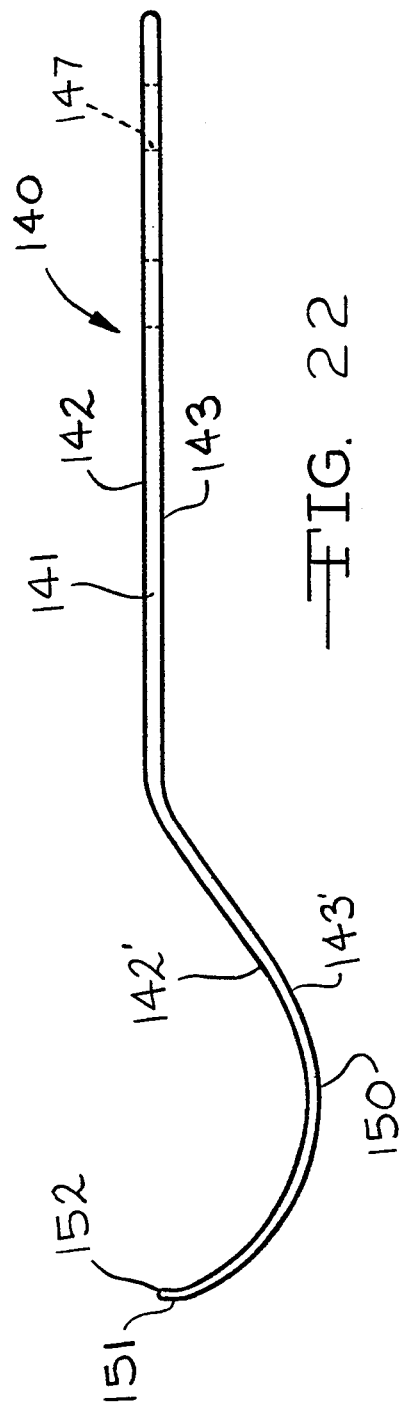
FIG. 22 is an elevational view of the unicompartmental retractor as shown in FIG. 21.

Referring now to FIGS. 7, 21 and 22, there is provided a unicompartmental retractor 140 which is designed as a shield to protect the collateral ligament 27 and posterior structures during unilateral proximal tibial osteotomy.

The unicompartmental retractor includes a handle 141 which has generally flat upper and lower parallel surfaces 142 and 143, respectively, and edges 144 and 145. The edges 144 and 145 are generally parallel in the area adjacent an arcuate free end 146. The handle 141 may have one or more holes 147 to provide a place for hooking weights thereto. At any desired point, tile edges 144 and 145 may taper toward a longitudinal axis 148.

Extending from the handle is an integral tip 150 having edges 144' and 145' which continue to taper toward a vertical plane passing through the longitudinal axis 148 (assuming the handle 141 is positioned with the upper and lower surfaces 142 and 143 in a horizontal plane). The tip 150 has upper and lower surfaces 142' and 143', respectively, which initially follow a straight line angled path downwardly from the handle 141 at an angle of approximately 45° +/−1.5°. It then joins with an arcuate portion where it curves upwardly on a radius of 1.5 inches +/−0.2 inch. The center of radius of such arc is positioned 0.35 inch +/−0.2 inch above the plane defined by the upper surface 142 of the handle and 2.26 inches +/−0.05 inch forward of tile juncture of the tip 150 with the handle 141. The arcuate section of the tip 150 has extending therefrom a short straight segment 151, 0.30 inch +/−0.02 inch in length, which is disposed at an angle of 5° +/−2° from vertical in a direction away from said handle 141 and terminates in an end 152 approximately 0.10 inch below the plane of the upper surface 142. The end 152 has a breadth of 0.30 inch +/−0.020 inch and perferably is rounded from the surface 142' to the surface 143'.

The handle 141 and the tip 150 up to approximately its lowest point of the arcuate section have a thickness of approximately 0.12 inch. However, the thickness in that area is not critical provided it is rigid enough to prevent excessive bending during use. From such lowest point to the end the thickness of the tip 150 tapers with a thickness at the end 152 of 0.060 inch +/−0.020 inch.

The angle of taper of the edges 144' and 145' is 5° +/−1° from a vertical plane passing through tile longitudinal axis 148 for a total included angle of 10° +/−2°.

In conducting the surgical procedure according to the method of the present invention, following incision of the knee K, the PCL tibial retractor 30 is inserted carefully between the distal femur 16 and the tibial plateau 12 with the prongs straddling on opposite sides of the posterior cruciate ligament 20 with the ends 43 of the prongs 40 resting against the posterior side of the lateral tibial condyle 13 and medial tibial condyle 14, respectively. The support section 38 of the PCL tibial retractor rests against the intercondylar notch 19 which acts as a fulcrum as the handle 31 is moved in the direction indicated by the arrow 48.

The lateral patellar retractor 50 is then inserted using the elongated center prong 64 as the lead along the lateral aspect of the lateral tibial condyle 13 with the support section 58 moving the adjacent soft tissue away from the incision to permit tibial osteotomy without risking damage to the surrounding soft tissue. After performing osteotomy on the tibial plateau, namely, the lateral tibial condyle 13 and medial tibial condyle 14, the posterior cruciate ligament retractor 70 is inserted on the medial side of the medial femoral condyle 18 while the collateral ligament retractor 90 is passed around the opposite side of such medial femoral condyle 18 meeting posteriorly to form a protective arc to protect the ligaments and hold them clear of the blade of the oscillating saw during osteotomy of the posterior portion of the medial femoral condyle 18. The instruments are reversed and placed around the lateral femoral condyle 17 during posterior osteotomy of such lateral femoral condyle.

The unicompartmental retractor 140 is inserted around the side and posterior aspect of the tibial condyle, either the lateral tibial condyle 13 or medial tibial condyle 14, in order to protect the collateral ligament and posterior structures during unilateral proximal tibial osteotomy.

The invention disclosed herein provides new and novel surgical instruments in the form of retractors and femoral distractor which provide maximum protection to critical soft tissue members during osteotomy and other procedures and permit new and effective surgical procedures to be performed.

I claim:

1. A posterior cruciate ligament retractor for use in performing knee surgery comprising:
   (a) a handle extending along a longitudinal axis;
   (b) an integral support extending downwardly from said handle when the portion of said handle adjacent thereto is in a horizontal position and following initially a curved path and then a straight line path, said integral support having spaced apart edges, said spaced apart integral support edges being parallel and each lying in a plane substantially parallel to said longitudinal axis; and
   (c) an integral tip extending from said integral support and following a curved path which is reverse in direction to the curved path of said integral support, said integral tip having a pair of edges, each converging inwardly toward one another directly from one of said integral support edges, said pair of edges tapering in a straight line path toward a vertical plane lying on said longitudinal axis and terminating in a point free end.

2. A posterior cruciate ligament retractor comprising:
   (a) a handle extending along a longitudinal axis;
   (b) an integral support extending downwardly from said handle when the portion of said handle adjacent thereto is in a horizontal position and following initially a curved Oath and then a straight line path, the breadth of said support being 0.43 inch +/−0.02 inch, and;
   (c) an integral tip extending from said integral support and following a curved path which is reverse in direction to the curved path of said integral support, said integral tip having edges tapering toward a vertical plane lying on said longitudinal axis and terminating in a pointed free end, said tip having a length of 1.10 inch +/−0.02 inch and two edges, each disposed at an angle of 4° +/−1° to vertical plane lying on said longitudinal axis, the end of said tip having a thickness of 0.045 inch +/−0.01 inch.

3. A posterior cruciate ligament retractor comprising:
(a) a handle extending along a longitudinal axis;
(b) an integral support extending downwardly from said handle when the portion of said handle adjacent thereto is in a horizontal position and following initially a curved path and then a straight line path; said integral support is disposed at an angle of 22° +/−1.5° from the adjacent handle portion and having a breadth of 0.43 inch +/−0.02 inch, and;
(c) an integral tip extending from said integral support and following a curved path which is reverse in direction to the curved path of said integral support, said integral tip having edges tapering toward a vertical plane lying on said longitudinal axis and terminating in a pointed free end, said tip having a length of 1.10 inch +/−0.02 inch and two edges, each disposed at an angle of 4° +/−1° to vertical plane lying on said longitudinal axis, the end of said tip having a thickness of 0.045 inch +/−0.01 inch.

* * * * *

UNITED STATES PATENT AND TRADEMARK OFFICE
CERTIFICATE OF CORRECTION

PATENT NO. : 5,397,330
DATED : March 14, 1995
INVENTOR(S) : W.E. Michael Mikhail It is certified that error appears in the above—identified patent and that said Letters Patent is hereby corrected as shown below:

On title page, item [76] "E. Michael Mikhail" should be
--W.E. Michael Mikhail--.

Column 1, line 39, "DD-215-46S-A" should be --DD-215-468-A--.

Column 3, line 66, "tile" should be --the--.

Column 4, line 15, "tile" should be --the--.

Column 6, line 6, "tile" should be --the--.

Column 7, line 65, "tile" should be --the--.

Column 8, line 47, "tile" should be --the--.

Column 9, line 24, "tile" should be --the--.

Column 9, line 59, "tile" should be --the--.

Column 10, line 62, "Oath" should be --path--.

Signed and Sealed this

Twenty-ninth Day of August, 1995

Attest:

BRUCE LEHMAN

*Attesting Officer*   *Commissioner of Patents and Trademarks*